United States Patent [19]

Stevens

[11] Patent Number: 4,686,023

[45] Date of Patent: Aug. 11, 1987

[54] SENSITIZED PHOTOCHEMICAL PREPARATION OF VITAMIN D

[75] Inventor: Richard D. S. Stevens, Toronto, Canada

[73] Assignee: Solarchem Research, Division of Brolor Investments, Ltd., Ontario, Canada

[21] Appl. No.: 801,853

[22] Filed: Nov. 26, 1985

[51] Int. Cl.$^4$ .............................. C07C 1/72; C07J 9/00
[52] U.S. Cl. ............................... 204/157.67; 260/397.2
[58] Field of Search .................................... 204/157.67

[56] References Cited

U.S. PATENT DOCUMENTS 4,265,822  5/1981  DeLuca et al. ................. 204/157.67

FOREIGN PATENT DOCUMENTS 0213210  9/1984  Fed. Rep. of Germany ....................... 204/157.67

Primary Examiner—Arthur P. Demers
Attorney, Agent, or Firm—Browdy and Neimark

[57] ABSTRACT

Tachysterol-2 or tachysterol-3 is photochemically converted in high yield to previtamin $D_2$ or previtamin $D_3$ respectively, by irradiation in the presence of anthracene as photosensitizer. The wavelength of irradiation is suitably about 375 nm. This irradiation may be performed upon the mixture of substances resulting from the prior photolysis of a starting material selected from ergosterol (for previtamin $D_2$) and 7-dehydrocholesterol (for previtamin $D_3$) with 240–265 nm wavelength light, i.e. a mixture containing the respective lumisterol, starting material and previtamin, as well as the respective tachysterol. Using the process of the invention, conversions of tachysterol to previtamin as high as 93% can be achieved, and overall conversions of ergosterol or 2-dehydrocholesterol to previtamin $D_2$ or previtamin $D_3$ respectively can be as high as 80%.

11 Claims, No Drawings

SENSITIZED PHOTOCHEMICAL PREPARATION OF VITAMIN D

FIELD OF THE INVENTION

This invention relates to photochemical synthesis, and more specifically to vitamin D synthesis, including both vitamin $D_2$ and vitamin $D_3$ and other hydroxylated vitamin D derivatives by appropriate irradiation of precursor materials.

BACKGROUND

Vitamin $D_3$ is commonly prepared, in commercial practice, by a process involving the photolysis of 7-dehydrocholesterol, to form an intermediate product previtamin $D_3$, which is then heated to convert it to vitamin $D_3$, thus:

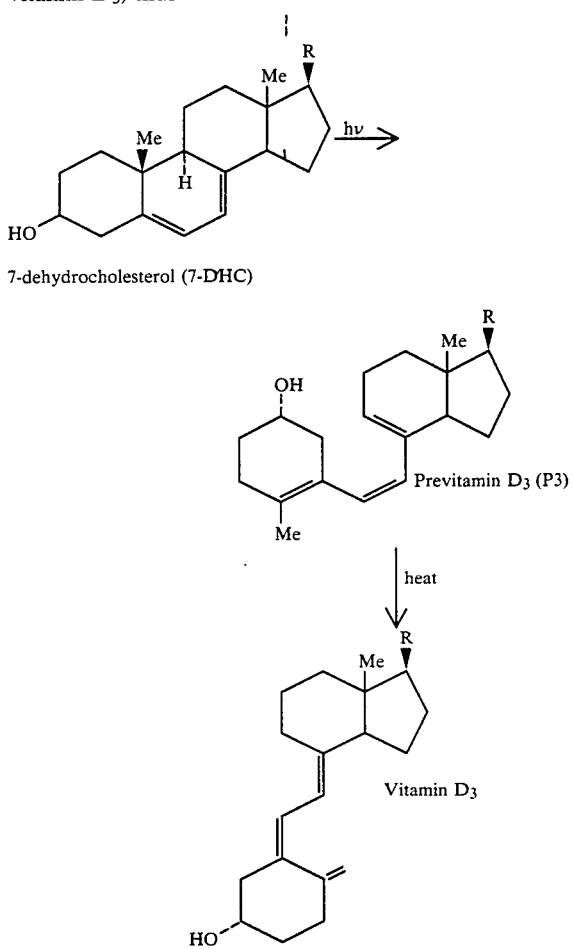

the group R in the above formula representing the branched alkyl chain of vitamin $D_3$, which is well known and remains unchanged in the reactions. Vitamin $D_2$ differs therefrom chemically only in minor respects relating to the nature of the branched alkyl group R. Ergosterol is an available natural material, while 7-DHC is commonly synthesized from cholesterol. The process as a whole is made more expensive by the relatively low yields of previtamin $D_3$ (pre-3) which may be obtained. Pre 3 is liable to undergo side photolysis reactions, to form lumisterol (L3) and tachysterol (T3). At least according to some of the published literature, the photolysis is often stopped at 30–40% conversion of the 7-DHC, when the concentration of Pre 3 in the mixture is at a maximum, the product mixture separated and recycled. Whilst the reactions of Pre 3 to form T3 or L3 are reversible, $D_3$ cannot be formed directly from either T3 or L3. The reaction system may be represented as follows:

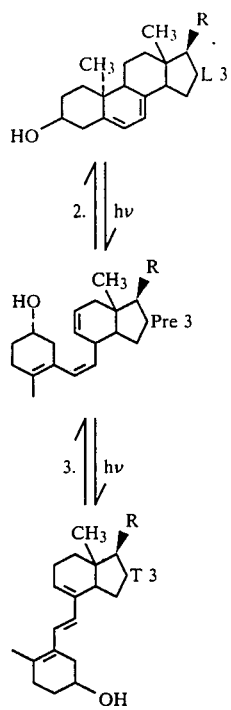

For a commercially successful and economic process, therefore, the system must be optically pumped so as to produce a maximum concentration of Pre 3 while minimizing the concentrations of L3, T3, and residual 7-DHC. In addition, it is of course desirable to minimize the energy costs for the irradiations.

BRIEF REFERENCE TO THE PRIOR ART

Malatesta et al, J. Am. Chem. Soc. 103, 6781–83, (1981) reported the results of studies of laser photolysis of 7-DHC at various wavelengths, and used a two-stage photolysis to engineer a desirable product distribution with improved yields. In a first stage, photolysis was conducted at 248 nm, and a product mixture containing 25.8% P3, 71.3% T3 and 2.9% unchanged 7-DHC was reportedly obtained. This product mixture was then submitted to photolysis at 337 nm using a nitrogen laser, to convert relatively large proportions of the T3 to P3, and reportedly obtain a product mixture containing 79.8% P3, 1.5% T3 and 8.8% 7-DHC. In another experiment, the second stage irradiation was conducted with irradiation from a YAG laser, wavelength 353 or 355 nm, and essentially similar results obtained. The irradiation times however are long, totalling over 4½ hours. This product mixture convert P3 to $D_3$. Similar work has been reported by Dauben and Phillips, J. Am. Chem. Soc. 104, 355 (1982). Dauben, et. al. report that on the basis of the spectral data of the four major irradiation products, the yield of vitamin D analogues should be maximized by using a first step, irradiation with light of either 254 nm or 300 nm wavelength, and a second step irradiation with light of wavelength 330 nm or greater. In practice, Dauben, et. al. in most experiments apparently used a broad band 350 nm Rayonet lamp for the second step irradiation, which probably emits over the 330–370 nm wavelength range, and a YAG laser with emission at 355 nm in another experiment. The best results reportedly were obtained with the broad band lamp.

Despite the fact that the Malatesta group and the Dauben group appear in some experiments to have used essentially the same irradiations (248 nm or 254 nm first stage, 355 nm YAG laser second stage), their results do not agree.

European Patent Application No. 0,130,509, F. Hoffmann-La Roche and Co. discloses a process for photochemical production of previtamin D from tachysterol, in which certain heterocyclic fused ring acid compounds, for example 2-(6-hydroxy-3-oxo-3H-thioxanthen-9-yl)benzene-sulphonic acid (sodium salt) are used as photosensitizer.

Snoeren. et. al. (1970) RECUEIL p.261 describe an investigation of photochemical isomerization of tachysterol to previtamin D using sensitizers in the reactant solution and radiation of wavelength 370 nm–430nm. They report fluorenone, benzil and anthraquinone to be effected sensitizers, but also report that anthracene, benzpyrene and azulene are not effective.

Denny, et. al. "Nouveau Journal de Chimie", vol. 2 No. 6 p.637 report the use of lower energy sensitizers in tachysterol-previtamin D conversion. They confirm the report that anthracene and benzpyrene are not effective sensitizers in this area.

At all stages of the irradiation, it has previously been considered highly desirable to reduce the formation of lumisterol, L3. This by-product is formed in larger quantities in the product mix when irradiation takes place at longer wavelengths.

SUMMARY OF THE INVENTION

The present invention provides a novel and practical process for producing previtamin $D_3$ from 7-dehydrocholesterol, previtamin $D_2$ from ergosterol and the like, by photolysis.

In accordance with the present invention, it has been found, contrary to previous reports, that anthracene can act as an efficient photosensitizer in the photochemical conversion of tachysterol-3 to previtamin $D_3$ and of tachysterol-2 to previtamin $D_2$, using radiation sources which emit significant energy in the region 290–400 nm. Ratios as high as 13:1 Pre 3 to T3 and overall yields in two stage irradiation of greater than 80% can be obtained. The sensitized photochemical conversion takes place in the substantial absence of oxygen.

Thus, in one aspect, the present invention provides a process for photochemical preparation of previtamin D from tachysterol which comprises irradiating tachysterol in the substantial absence of free oxygen with radiation of appropriate wavelength in the presence of an effective amount of anthracene as photosensitizer.

In another aspect, the present invention provides a process of photochemical preparation of previtamin $D_3$ or previtamin $D_2$ from the appropriate starting material selected from 7-dehydrocholesterol and ergosterol, in two irradiation stages, which comprises, in a first stage, irradiating the selected starting material with radiation in the wavelength range 240–265 nm to effect substantial conversion of the starting material, and in a second stage irradiating at least the tachysterol containing a portion of the product mix from the first stage in the substantial absence of free oxygen at an appropriate wavelength in the presence of anthracene or photosensitizer.

DESCRIPTION OF THE PREFERRED EMBODIMENTS

The radiation in the presence of anthracene can if desired be solar radiation, direct or appropriately filtered. Preferably the radiation in the presence of anthracene contains a significant component of wavelength about 375 nm, and no significant radiation below about 350 nm.

Whilst it is not intended that the scope or operation of the invention should be limited by any particular theory of mechanism or operation, it appears that, under appropriate irradiation e.g. at 375 nm, anthracene absorbs the radiation strongly, and is raised from its ground state to an excited singlet and hence by efficient intersystem crossing to an excited triplet state, this acquired energy is then transferred from the anthracene to form a triplet state of tachysterol, which in turn converts to previtamin D. In any event, irradiation above wavelength about 360 nm does not affect tachysterol directly, or other steroids closely related thereto. Accordingly, the process of the present invention can advantageously be practiced on a steroid mixture containing tachysterol, e.g. a mixture of 7-dehydrocholesterol or ergosterol, lumisterol, tachysterol and previtamin D, such as that commonly obtained in a commercial or first stage irradiation of 7-DHC or ergosterol at wavelength 240–265 nm. Irradiation at 375 nm in the presence of anthracene selectively converts the tachysterol to previtamin $D_3$.

In one aspect, the process of the present invention is a two-stage process, the first stage being irradiation of the selected starting material at 240–265 nm and the second stage being irradiation in the 290–400 nm range, most preferably at about 375 nm in the presence of anthracene. Solar radiation, direct or filtered, can be used in the second stage. The second stage irradiation should be of wavelength within the absorption spectrum of anthracene and can also be within the absorption spectrum of the other components of the mixture as well, namely tachysterol, lumisterol and the previtamin D. Provided that the anthracene absorbs a substantial portion of the available useful radiation, so as to cause the photochemical conversion of the tachysterol as above, and provided that the anthracene is present in sufficient quantities for this purpose, effective and selective photochemical conversion of tachysterol will occur.

In practice, the photochemical conversions are preferably conducted in solution in organic solvents such as ether, which are inert towards the reactants and products and non-absorbing at the wavelength utilized. The amount of anthracene which is present can be anywhere within the range 0.001 grams per liter up to a saturated solution of anthracene in the chosen solvent, which in the case of diethyl ether a solvent is 5 grams per liter. Only very small amounts of anthracene need to be present, preferably in the range 0.001 gm/l to 0.046 gm/l, although larger amounts are not harmful. In many instances, the amount of anthracene will be limited by its solubility in the chosen solvent. The radiation intensity and exposure time are adjusted so as to obtain equilibrium in the photochemical conversion of tachysterol to Previtamin without loss of mass balance.

For ease and simplicity of description, the invention is described below with reference to the conversion of 7-DHC to previtamin $D_3$ with vitamin $D_3$ as objective.

It is however to be understood that the invention also applies to conversion of ergosterol to P2 with $D_2$ as objective, and the conversion of other analogous products where the 9, 10-bond of the cholesterol steroid nucleus is subjected to photochemical scission followed by photochemical cis-trans isomerisation of the resultant C—C unsaturated chain. Such analogous products may have additional chemical substituents thereon, provided the substituents do not interfere in the photochemical conversions. Such processes are within the scope hereof.

Another aspect of the present invention relates to recycle of the by-products of the second stage irradiation to the first stage irradiation. It has been found that lumisterol (L) can be photochemically converted by irradiation with light in the approximate wavelength range 240–265 nm to a product mixture containing substantial amounts of previtamin D and tachysterol, and very little residual L. Moreover, such a process can be conducted in the presence of 7-DHC or ergosterol. Accordingly, the present invention provides a process of separating previtamin D from the by-products (largely tachysterol and lumisterol) of a process of irradiation of a product mixture containing previtamin D and tachysterol, adding said by-products to 7-DHC or ergosterol, and irradiating the mixture with light in the approximate wavelength the 240–265 nm. In this way, the lumisterol previously regarded as a troublesome by-product of little practical use, can be converted by recycle through the two-stage process, firstly to tachysterol in the first stage, and thence to previtamin D in the second stage. The economics of the overall process are thus significantly enhanced. In practice, the reactant mixture is preferably dissolved in a suitable solvent such as diethyl ether, and held in a suitably radiation transmissive container. Such solutions are preferably appropriately deoxygenated, to reduce formation of oxidative by-products during irradiation. The solution may be arranged to flow continuously or semi-continuously through an appropriately designed such container on exposure to irradiation, to provide an economical practical process. The first stage of irradiation may be conducted on a suspension or solution of 7-DHC, e.g. a solution thereof in diethyl ether.

The temperature at which the irradiations take place are suitably between $-40°$ C. and about $50°$ C., between $0°$ C. and room temperature being normally suitable. This is determined to a large extent by the nature of the reactant which is being irradiated. For example, when irradiating ether solutions, the temperatures should be kept low, to avoid problems with volatilized ether. When less volatile, higher boiling solvents are employed, higher temperatures can be adopted, and may even be advantageous, in encouraging the conversion of previtamin 3 to vitamin $D_3$ and hence reducing side reactions thereof.

As a final step in the process, previtamin 3 is heated to produce vitamin $D_3$. This step is known in the art, and suitably involves heating to a temperature of $50°$–$100°$ C., suitably about $70°$ C. for a sufficient length of time to effect the conversion, followed by product extraction and separation.

The invention is illustrated in the following specific examples.

EXAMPLE 1

A solution of 7-dehydrocholesterol (7-DHC) in diethyl ether was prepared, at a concentration of 1 g/liter, and passed through a flow cell at a rate of 4.8 ml/minute. As it passed through the cell, it was irradiated with radiation of wavelength 254 nm using a low pressure mercury lamp at an average intensity of 2.7 m.watts/cm$^2$ (as determined by an OAI exposure monitor equipped with a 260 nm probe).

The resultant solution was sampled and analyzed by HPLC, and found to possess the following fractional mass distribution:
Previtamin $D_3$—0.222
Lumisterol-3—0.020
Tachysterol-3—0.692
7-DHC—0.071
Mass balance—1.005.

Anthracene was then added to this product solution, in an amount of 0.029 gm/l, and the mixture then irradiated in a batch reactor with black lamp radiation of wavelength 350–400 nm, using two General Electric 40 BL lamps placed 5.5 inches from the reactor. The time of irradiation was 18 minutes. The product mixture was then analyzed by HPLC, and the following reactant-product mass fractional distribution obtained:
Previtamin $D_3$—0.785
Lumisterol $L_3$—0.021
Tachysterol $T_3$—0.007
7-DHC—0.061
Mass balance—0.874.

A high photochemical conversion of tachysterol $T_3$ to previtamin $D_3$ has thus occurred in the second stage irradiation, sensitized by the anthracene.

EXAMPLE 2

The procedures of Example 1 were repeated, except that, in the second stage, the time of irradiation was 14 minutes. The following reactant-product mass fractional distributions were obtained:
1st Stage
Previtamin $D_3$—0.220
Lumisterol-3—0.016
Tachysterol-3—0.686
7-DHC—0.076
Mass balance—0.998.
2nd Stage
Previtamin $D_3$—0.811
Lumisterol-3—0.018
Tachysterol-3—0.056
7-DHC—0.060
Mass Balance—0.945.

EXAMPLE 3

The procedures of example 1 were essentially repeated except that sunlight was used in the second stage and the time of irradiation was 120 minutes. The following reactant-product mass fractional distributions were obtained:
1st Stage
Previtamin $D_3$—0.229
Lumisterol -3—0.019
Tachysterol -3—0.696
7-DHC—0.053
Mass Balance—0.997.
2nd Stage
Previtamin $D_3$—0.806
Lumisterol -3—0.049
Tachysterol -3—0.024
7-DHC—0.053
Mass Balance—0.932.

I claim:

1. A process for achieving substantial photochemical conversion of tachysterol to previtamin D which comprises irradiating tachysterol in the presence of lumisterol, previtamin D and one of ergosterol and 7-dehydrochlolesterol, in the substantial absence of free oxygen, with radiation having a signficant energy in the region 290–400 nm and in the presence of an effective amount of anthracene as photosensitizer, the wavelength of said irradiation being within the absorption spectrum of antracene and within the absorption spectra of tachysterol, lumisterol and the previtamin D, the anthracene concentration in the reactant mixture being sufficient to ensure that anthracene absorbs a substantial portion of the available, useful radiation.

2. The process of claim 1 wherein tachysterol $T_3$ is irradiated in the presence of anthracene to produce previtamin $D_3$.

3. The process of claim 2 wherein the tachysterol -3 is irradiated in the presence of 7-dehydrocholesterol, lumisterol-3 and previtamin $D_3$.

4. The process of claim 3 wherein the mixture of tachysterol -3, 7-dehydrocholesterol, lumisterol-3 and previtamin $D_3$ is the product mix resulting from the photochemical reaction of 7-dehydrocholesterol, optionally in admixture with tachysterol -3 and lumisterol-3, under the influence of irradiation of wavelength in the approximate range 240–265 nm.

5. A process of photochemical preparation of previtamin $D_3$ or prevention $D_2$ from the appropriate starting material selected from 7-dehydrocholesterol and ergosterol, in two irradiation stages, which comprises, in a first stage, irradiating the selected starting material with radiation in the wavelength range 240–265 nm to effect at least partial conversion of the starting material to a tachysterol - containing product mix, and in a second stage irradiating at least some of the tachysterol containing portion of the product mix from the first stage in the substantial absence of free oxygen at an appropriate wavelength in the presence of anthracene as photosensitizer, to effect substantial photochemical conversion of said tachysterol to the respective previtamin D3 or previtamin D2.

6. The process of claim 5 wherein the second stage irradiation is conducted using radiation of wavelength about 375 nm.

7. The process of claim 5 wherein the wavelength of said second stage irradiation is within the absorption spectrum of anthracene and within the absorption spectrum of tachysterol and the previtamin D, the anthracene concentration in the second stage reactant mixture being sufficient to ensure that anthracene and tachysterol together absorb substantially all the available useful radiation.

8. The process of claim 5 wherein by-product lumisterol produced in the first stage irradiation is further subjected to radiation of wavelength in the approximate range 240–265 nm, to convert substantial portion thereof to the appropriate previtamin.

9. The process of claim 8 wherein said by-product lumisterol is recycled to the first stage irradiation, and then irradiated in the presence of the selected starting material with radiation of wavelength in the approximate range 240–265 nm.

10. The process of claim 5 wherein the starting material is 7-dehydrocholesterol.

11. The process of claim 5 wherein the starting material is ergosterol.

* * * * *

UNITED STATES PATENT AND TRADEMARK OFFICE
CERTIFICATE OF CORRECTION

PATENT NO. : 4,686,023

DATED : August 11, 1987

INVENTOR(S) : Stevens, Richard D.S.

It is certified that error appears in the above-identified patent and that said Letters Patent is hereby corrected as shown below:

Column 3, Line 23: Change "effected" to --effective--.

Claim 1, line 10: Change "antracene" to --anthracene--.

Claim 5, Line 29: Change "prevention" to --previtamin--.

Signed and Sealed this

Twelfth Day of September, 1989

Attest:

DONALD J. QUIGG

*Attesting Officer*   Commissioner of Patents and Trademarks